US006835377B2

(12) United States Patent
Goldberg et al.

(10) Patent No.: US 6,835,377 B2
(45) Date of Patent: Dec. 28, 2004

(54) OSTEOARTHRITIS CARTILAGE REGENERATION

(75) Inventors: Victor M. Goldberg, Gates Mills, OH (US); Arnold I. Caplan, Cleveland Heights, OH (US); Francis P. Barry, Baltimore, MD (US); David J. Fink, Baltimore, MD (US); Daniel R. Marshak, Lutherville, MD (US); James S. Burns, Annapolis, MD (US)

(73) Assignee: Osiris Therapeutics, Inc., Baltimore, MD (US)

( * ) Notice: Subject to any disclaimer, the term of this patent is extended or adjusted under 35 U.S.C. 154(b) by 559 days.

(21) Appl. No.: 09/078,531

(22) Filed: May 13, 1998

(65) Prior Publication Data

US 2002/0110544 A1 Aug. 15, 2002

(51) Int. Cl.[7] .................................................. C12N 5/00
(52) U.S. Cl. ....................... 424/93.7; 435/366; 435/372
(58) Field of Search ........................ 424/93.7; 435/366, 435/372

(56) References Cited

U.S. PATENT DOCUMENTS

| | | | |
|---|---|---|---|
| 4,642,120 A | 2/1987 | Nevo et al. | |
| 5,053,050 A | 10/1991 | Itay | |
| 5,206,023 A | 4/1993 | Hunziker | |
| 5,226,914 A | 7/1993 | Caplan et al. | |
| 5,326,357 A | 7/1994 | Kandel | |
| 5,399,493 A | 3/1995 | Emerson et al. | |
| 5,486,359 A | 1/1996 | Caplan et al. | |
| 5,716,616 A | 2/1998 | Prockop et al. | |
| 5,736,396 A | 4/1998 | Bruder et al. | |
| 5,906,934 A | * 5/1999 | Grande et al. | 435/325 |

OTHER PUBLICATIONS

Pettipher et al., PNAS 83: 8749–87–53 (Nov. 1986).*
Bruder, S.P., et al., "Mesenchymal Stem Cells in Bone Development, Bone Repair, and Skeletal Regeneration Therapy," *Journal of Cellular Biochemistry*, 56:283–294(1994).

Joyce, M.E., et al., "Transforming Growth Factor–β and the Initiation of Chondrogenesis and Osteorogenesis in the Rat Femur," *The Journal of Cell Biology*, 110: 2195–2207(1990).

Bradham, D. M., et al., "Mesenchymal Cell Chondrogenesis is Stimulated by Basement Membrane Matrix and Inhibited by Age–Associated Factors," *Matrix Biology*, 14:561–571 (1994).

Solursh, M., et al., "Extracellular Matrix Mediates Epithelial Effects on Chonodrgenesis in Vitro," *Developmental Biology*, 105:451–457 (1984).

Hunziker, E.B. and Rosenberg, L.C., "Repair of Partial–Thickness Defects in Articular Cartilage: Cell Recruitment from the Synovial Membrane," *The Journal of Bone and Joint Surgery*, 78–A(5):721–733 (1996).

* cited by examiner

*Primary Examiner*—Jean C. Witz
(74) *Attorney, Agent, or Firm*—Elliot M. Olstein; Raymond J. Lillie

(57) ABSTRACT

For repair of cartilage damaged as part of the degenerative effects of osteoarthritis, the inventors have found that the human mesenchymal stem cell approach makes it possible to: (1) regenerate both shallow cartilage chondral defects and full thickness cartilage defects (osteochondral lesions); (2) broaden the suitable clinical population to routinely include middle-aged patients; (3) eliminate the use of autologous tissue grafts (mature cartilage and the periosteal covering) to repair an articular cartilage injury; (4) regenerate other types of injured cartilage such as patellar and spinal disk cartilage; (5) regenerate articular joint cartilage in older patients with osteoarthritis; and (6) form new cartilage and subchondral bone which fully integrate into the adjacent normal tissue.

19 Claims, 13 Drawing Sheets

OSTEOARTHRITIS CARTILAGE REGENERATION

BACKGROUND OF THE INVENTION

Arthritis is the most common chronic musculoskeletal disorder, affecting nearly 23 million patients or 9% of the U.S. population, with osteoarthritis (OA) comprising about 70% of that patient population. Arthritis is the leading age-related medical condition among women and ranks as the second most common such condition among men over 45 years of age. Deformities or orthopaedic joint impairment rank sixth among chronic disorders causing activity limitations.

As an age-related condition, the continued projected growth of the elderly as a percentage of the total population will increase the prevalence of arthritis. Increasing longevity of the elderly population will further accelerate the incidence of age-related conditions such as arthritis. A significant portion of elderly arthritis sufferers are afflicted seriously enough to be considered disabled. Through the year 2000, the disabled elderly population is expected to increase to over 7 million (18% of elderly) patients, and more than double to 15–20 million over the subsequent fifty years.

Hospitalizations resulting from arthritis are the second highest admissions category (8–10% of patients), followed by other orthopaedic impairments as the fourth leading category. Each year, approximately 1.3 million patients are admitted to U.S. hospitals for arthritis treatment, 85% of which are osteoarthritis patients.

Of the half million arthroplasty procedures performed annually in the U.S., approximately 80% are performed on the hip and knee. Osteoarthritis is estimated to account for 50% of hip arthroplasties and over 80% of knee arthroplasties. Hip and knee osteoarthritis are the two most common forms of joint cartilage degeneration. Both forms of osteoarthritis occur most commonly in patients over 50 years old. Hip osteoarthritis is characterized by movement pain, joint stiffness and eventually deformity of the hip.

Osteoarthritis can be a primary degenerative process, result from childhood hip disorders, or as secondary to adult injury, infection, endocrine/metabolic disorders or bone dysplasia. Depending on the patient's age, their range of hip motion and clinical presentation, current operative procedures range from arthrodesis in young patients and osteotomy in patients under 60 years with reasonable hip motion, to hemi-, total, resection and cup arthroplasty. Knee osteoarthritis is characterized by pain, joint swelling, stiffness, motion loss and eventually deformity. As with the hip, knee osteoarthritis may be a primary degenerative process or result from a single or repeated knee injuries.

Osteoarthritis is a progressively degenerative disease, resulting in increasing pain, impairment and ultimately disability. While the available treatments seek to ameliorate pain or improve mobility, these treatments rarely modify the course of the disease, but rather attend to its consequences. For early stage osteoarthritis, treatment is largely limited to addressing the symptoms of inflammation with non-steroidal anti-inflammatory drugs, steroids for acute exacerbation and some use of the more toxic Disease-Modifying Arthorheumatic Drugs (DMARDS, e.g. gold salts, penicillamine, and methotrexate). Clinical reports indicate that even the newest DMARDS, such as tenidap, will not materially improve the clinical outcomes. None of these treatments stop the progression of the condition nor regenerate damaged cartilage.

Depending on the patient's age and health status, current operative treatment involves proximal tibial or distal femoral osteotomy, unicompartmental knee replacement, or total knee arthroplasty. Evolving treatment procedures include arthroscopic debridement, abrasion/drilling of chondral defects and articular cartilage allografts.

No approaches currently exist to adequately treat arthritic patients, despite the large number of patients who could benefit from treatments which are less invasive than end-stage joint replacement. Once the condition has progressed to substantial articular cartilage damage, none of the currently available approaches are adequate.

Various groups have initiated cell seeding-absorbable matrix projects using mature differentiated chondrocytes. One such group is developing a cell-seeded absorbable matrix for non-weight bearing cartilage, while another is using a purified bovine collagen matrix for meniscal repair.

The approach of yet another group is a chondrocyte-seeded collagen matrix for articular cartilage repair. Others are investigating a yearly, and very costly multi-injection regimen of hydroxyapatite into the synovium to decrease pain and to delay arthroplasty in osteoarthritis patients.

Various reports of progress in cartilage repair demonstrate that partial repair of shallow joint cartilage injury may be feasible in younger patients. Using a technique which incorporates culture expanded mature cartilage cells (chondrocytes), these procedures provide encouraging initial results as to the potential role for cell therapy in cartilage repair. Despite these various attempts, cartilage repair is not yet possible.

SUMMARY OF THE INVENTION

As observed in arriving at the present invention, clinical acceptance will require more sophisticated cell therapy approaches designed to recapitulate the complete sequence of tissue-forming events—that is, starting with tissue progenitor cells (human mesenchymal stem cells or hMSCs) which form cartilage, bone, muscle, bone marrow stroma, ligament, tendon and connective tissue prenatally, and applying the same technology to the regeneration of injured and diseased tissue in adults.

Human mesenchymal stem cell technology provides not only multiple opportunities to regenerate cartilage, but other mesenchymal tissue as well, including bone, muscle, tendon, marrow stroma and dermis. The regeneration of cartilage and other injured or diseased tissue is achieved by administration of an optimal number of human mesenchymal stem cells to the repair site in an appropriate biomatrix delivery device, without the need for a second surgical site to harvest normal tissue grafts. Furthermore, opportunities also exist to use human mesenchymal stem cell technology for gene therapy, cancer treatment, bone marrow transplantation, and for the treatment of osteoporosis and osteoarthritis.

For repair of cartilage damaged as part of the degenerative effects of osteoarthritis, the present inventors have found that the human mesenchymal stem cell approach makes it possible to: (1) regenerate both shallow cartilage chondral defects and full thickness cartilage defects (osteochondral lesions); (2) broaden the suitable clinical population to routinely include middle-aged patients; (3) eliminate the use of autologous tissue grafts (mature cartilage and the periosteal covering) to repair an articular cartilage injury; (4) regenerate other types of injured cartilage such as patellar and spinal disk cartilage; (5) regenerate articular joint cartilage in older patients with osteoarthritis; and (6) form new cartilage and subchondral bone which fully integrate into the adjacent normal tissue.

The process of developing the present invention focused on the use of autologous mesenchymal stem cells for the regeneration of stable hyaline cartilage in affected joints. The articular cartilage of the knee and hip joints was the target of initial focus because the greatest morbidity and debilitating conditions in osteoarthritis arise from degeneration or degradation of these joints in the leg.

The most promising approach to articular cartilage repair appears to be the use of autologous mesenchymal stem cells, which are osteochondral precursors. Mesenchymal stem cells for articular cartilage repair are combined with a controlled-resorption biodegradable matrix, preferably collagen-based products. These mesenchymal stem cell-matrix implants initiate, de novo, tissue formation, and maintain and stabilize the articular defect during the repair process. In addition to gels, the types of biomatrix materials that may be used include sponges, foams or porous fabrics that form a three-dimensional scaffold for the support of mesenchymal stem cells. These materials may be composed of collagen, gelatin, hyaluronan or derivatives thereof, or may consist of synthetic polymers, or may consist of composites of several different materials. The different matrix configurations and collagen formulations will depend on the nature of the cartilage defect, and include those for both open surgical and arthroscopic procedures.

Several formulations of autologous, culture-expanded mesenchymal stem cells that serve as the basis of therapies for osteoarthritis are contemplated, depending on the stage, joint location, and severity of the disease. They are (1) a gel formulation that can be applied to osteochondral defects during arthroscopy; (2) an injectable cell suspension for delivery directly to the synovial space; and (3) a molded mesenchymal stem cell-biomatrix product to re-surface joint surfaces in advanced cases.

The methods, compositions and implant devices of the invention are particularly suited for established conditions where superficial chondral or osteochondral defects can be diagnosed, but prior to the point where there is widespread joint instability and bone destruction. A characteristic indicator of chondral defect is a visibly altered gait or use of the joint to accommodate the discomfort or stiffness resulting from tissue damage, and the objective of treatment is to regenerate full thickness articular cartilage at the site of the defects to thereby prevent the joint destabilization and rapid joint destruction which are common sequelae of advanced osteoarthritis.

Patients ranging in age from 30–50 years with one or more well-defined articular cartilage lesions (as determined by imaging modalities or diagnostic arthroscopy) are ideal candidates for treatment in accordance with the invention. The need for advanced surgical intervention involving osteotomy or total joint arthroplasty can be deferred or even obviated.

Administration is by application of culture-expanded (preferably autologous) human mesenchymal stem cells in a biodegradable collagen and/or fibrin matrix implant and/or blood serum clots to the affected joint. Application typically involves an arthroscopic procedure, which may include debridement of the defect prior to implantation of the human mesenchymal stem cell matrix. Within six to twelve weeks following implantation, the graft develops into fill thickness cartilage with complete bonding to the subchondral bone.

Approximately a month prior to the initial treatment of the patient, a bone marrow aspirate (e.g., approximately 10–20 ml) is obtained from the patient's medial posterior iliac crest using standard aseptic techniques in an out-patient procedure. A Bone Marrow Collection and Transport Kit, described herein, provides most or all of the material needed for safe and efficient collection, identification, and transportation of the collected bone marrow. The double-sealed collection vessel is refrigerated until ready for human mesenchymal stem cell processing. A single aspirate sample can be culture-expanded sufficiently to provide material for multiple lesions (4–6) during one or several arthroscopic procedures. The cryopreservation techniques described herein permit retention of that portion of the aspirate that is not needed currently until it is required.

In a preferred embodiment, the implant is a two-component product consisting of a culture-expanded human mesenchymal stem cell suspension or cryopreserved human mesenchymal stem cells in one sterile transport device and a flowable collagen matrix in another sterile transport device. The contents of the two transport devices are admixed in a combined or third separate sterile implant chamber (closed system) which attaches by means of custom couplers (supplied with the procedure tray) to fit standard arthroscopes. The implant chamber provides the means to freshly mix human mesenchymal stem cells with biomatrix at the time of the operative procedure. The implant chamber is maintained for a sufficient gelation time for the cell-matrix to achieve the proper viscosity, and allows the orthopaedist or the rheumatologist to adjust the procedure and/or implant volume to conform to the actual lesion configuration.

BRIEF DESCRIPTION OF THE DRAWINGS

FIG. 1A shows a cross-section of the hMSC pellets as described in Example 1, at 10× magnification.

FIG. 1B shows a cross-section of the hMSC pellets, maintained in culture in the presence of dexamethasone and TGF-β3 as described in Example 1, at 20× magnification.

FIG. 1C shows a cross-section of the hMSC pellets maintained in culture in the presence of dexamethasone and TGF-β3 as described in Example 1 at 40× magnification.

FIG. 1D shows a section of the same pellets, stained in control reactions without the addition of primary antibody, at 10× magnification.

FIG. 1E shows a section of the same pellets, stained in control reactions without the addition of primary antibody, at 20× magnification.

FIG. 1F shows a section of the same pellets, stained in control reactions without the addition of primary antibody, at 40× magnification.

FIG. 2A shows a cross-section of the hMSC pellets maintained in culture without TGF-β3 as described in Example 2 at 10× magnification.

FIG. 2B shows a cross-section of hMSC pellets maintained in culture without TGF-β3 as described in Example 2 at 20× magnification.

FIG. 2C shows a cross-section of the hMSC pellets maintained in culture without TGF-β3 as described in Example 2 at 40× magnification.

FIG. 2D shows a section of the same pellets, stained in control reactions without the addition of primary antibody, at 10× magnification.

FIG. 2E shows a section of the same pellets, stained in control reactions without the addition of primary antibody, at 20× magnification.

FIG. 2F shows a section of the same pellets, stained in control reactions without the addition of primary antibody, at 40× magnification.

FIG. 3A shows the MALDI-TOF mass spectrum of pig aggrecan G1 domain collected using sinapinic acid matrix. The peak labeled 1 corresponds to monomeric pig aggrecan G1 domain. Peaks 2, 3 and 4 correspond to the dimer, trimer and tetramer, respectively, of the molecule.

FIG. 3B shows the spectrum obtained for an aggrecan G1 isolated from human osteoarthritic tissue. The peak labeled 1 corresponds to human aggrecan G1 fragment generated in the cartilage tissue in vivo. Peak 2 corresponds to link protein.

FIG. 3C shows the same sample after reduction and carboxymethylation and removal of keratan sulfate chains by treatment with keratanase. Peak 1 corresponds to aggrecan G1 after removal of keratan sulfate chains. Peak 2 corresponds to link protein.

FIG. 4A shows the implant stained with toluidine blue, at low magnification (2×).

FIG. 4B shows the implant stained with toluidine blue at 10× magnification.

FIG. 4C is a section of the MSC implant stained with chondroitin-4-sulfate (antibody 3B3) (10×).

FIG. 4D is a section of the MSC implant stained with chondroitin-6-sulfate (ZB6) (10×).

FIG. 4E is a section of the MSC implant stained with keratan sulfate (5D4) (10×).

FIG. 4F is a section of the MSC implant stained with link protein (8A4) (10×).

FIG. 4G is a section of the MSC implant stained with collagen type n (C4F6) (10×).

FIG. 5B is a higher magnification of FIG. 5A.

FIG. 6A shows fluorescence staining; FIG. 6B shows gross appearance.

DETAILED DESCRIPTION OF PREFERRED EMBODIMENTS

Figure 1A:
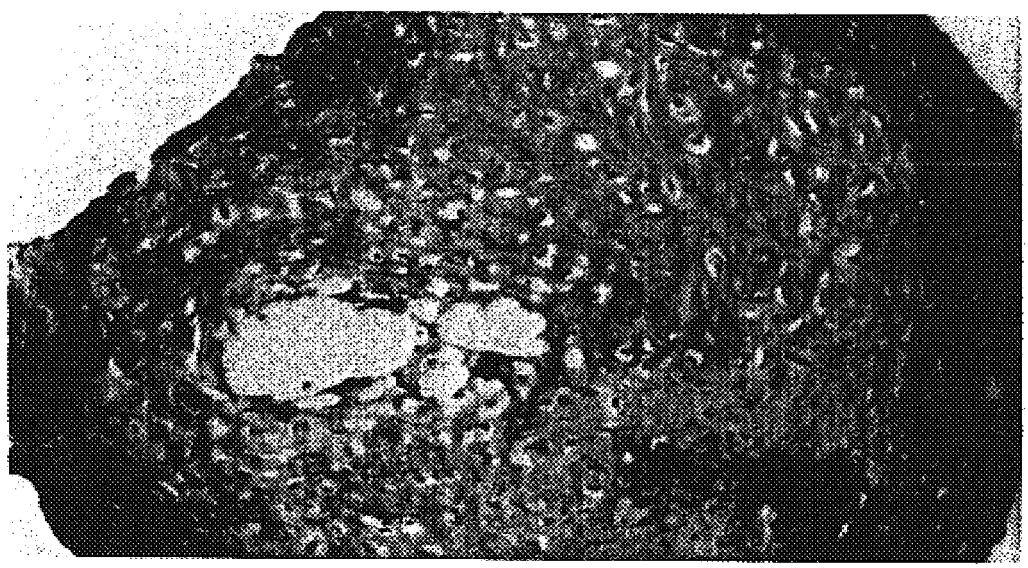
FIGS. 1A–1F show the effect of TGFβ on in vitro chondrogenesis of human bone marrow-derived mesenchymal stem cells.
Figure 1B:
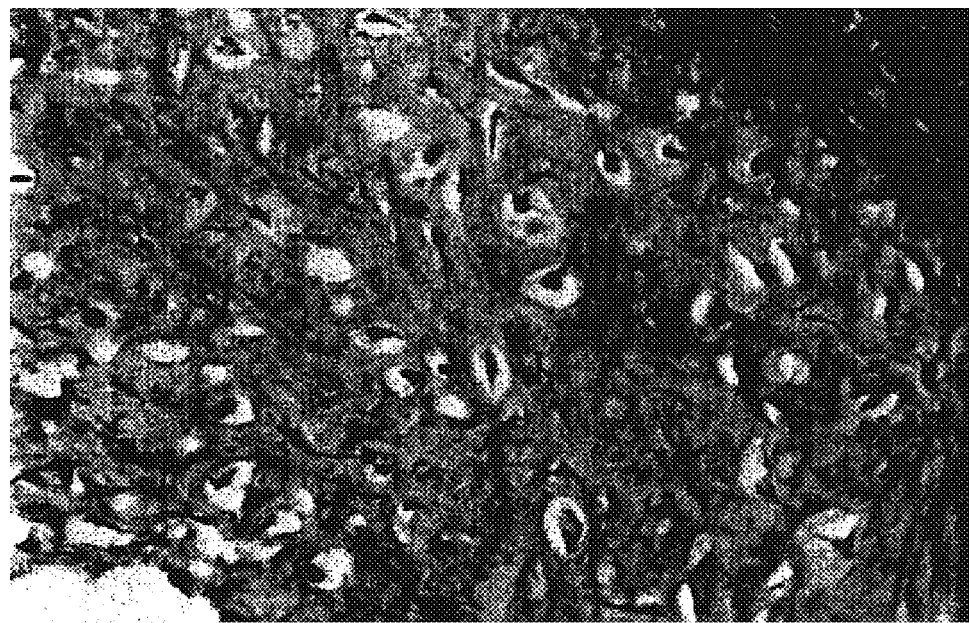
Figure 1C:
Figure 1D:
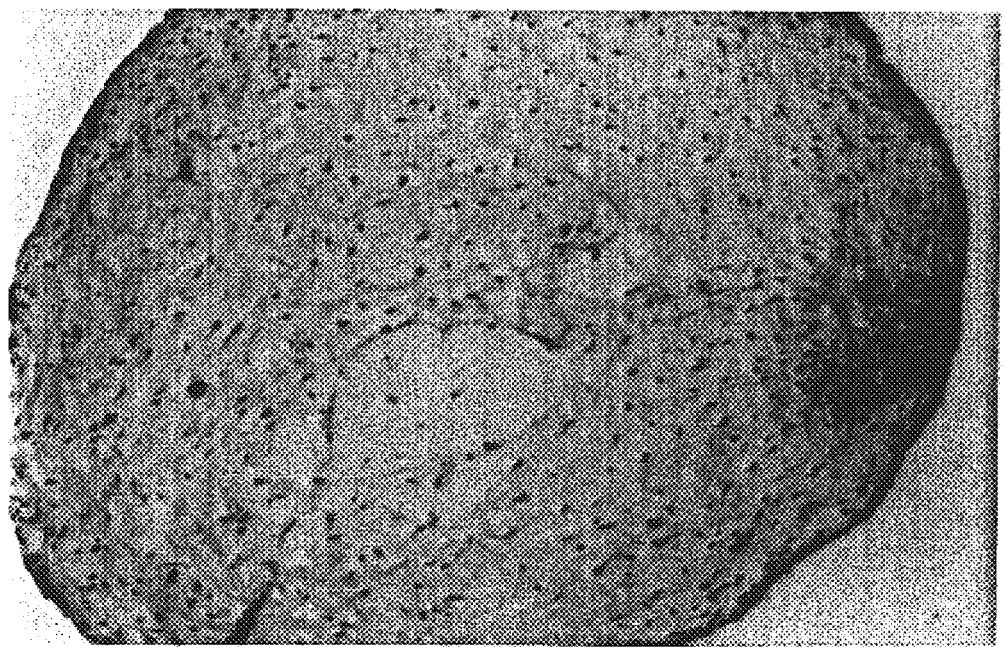
Figure 1E:
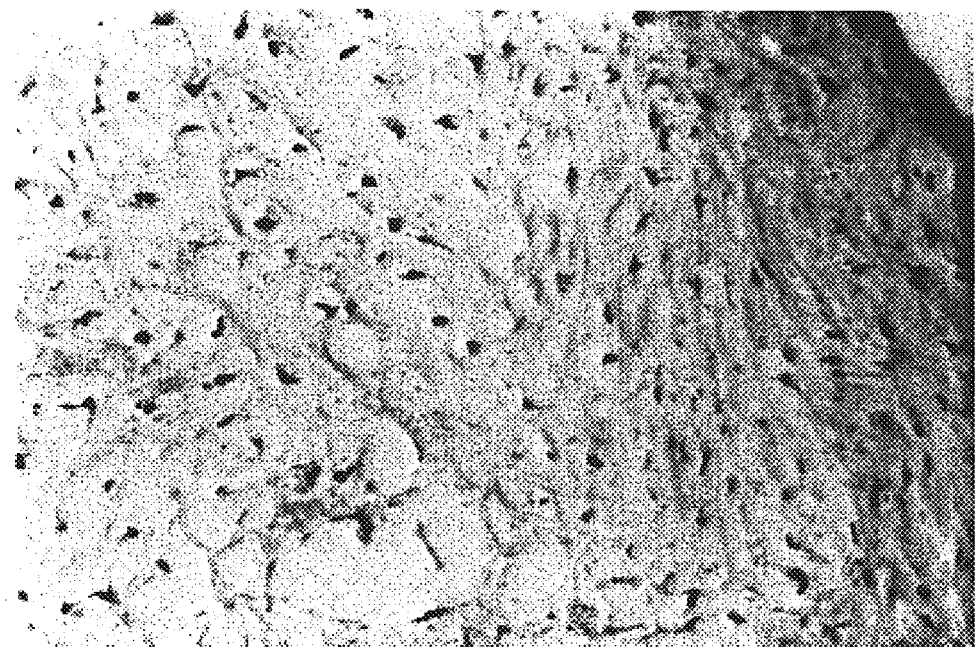
Figure 1F:
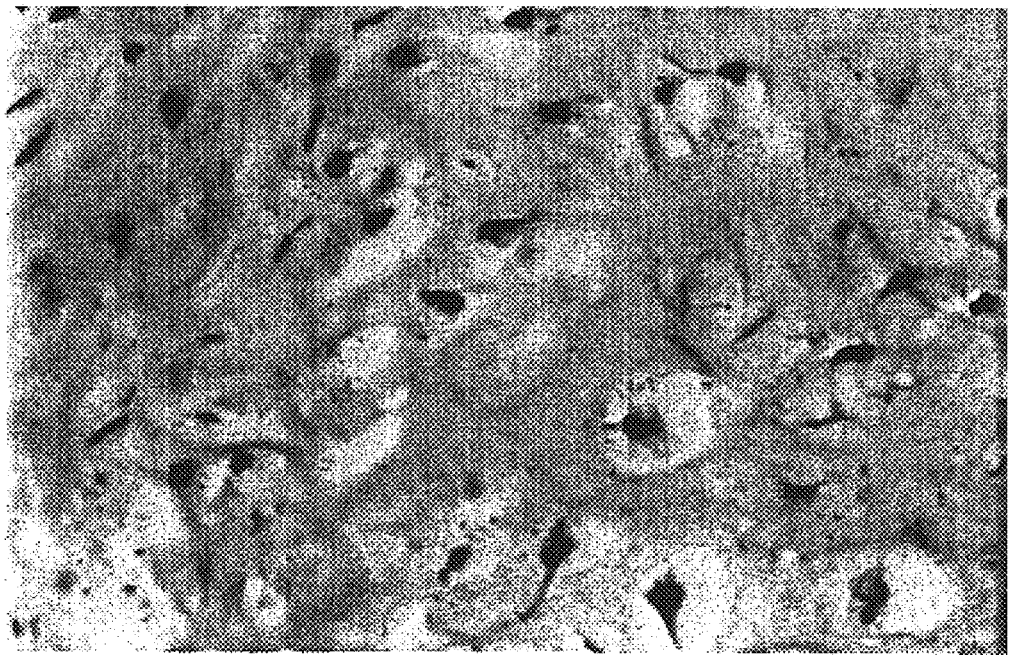
Figure 2A:
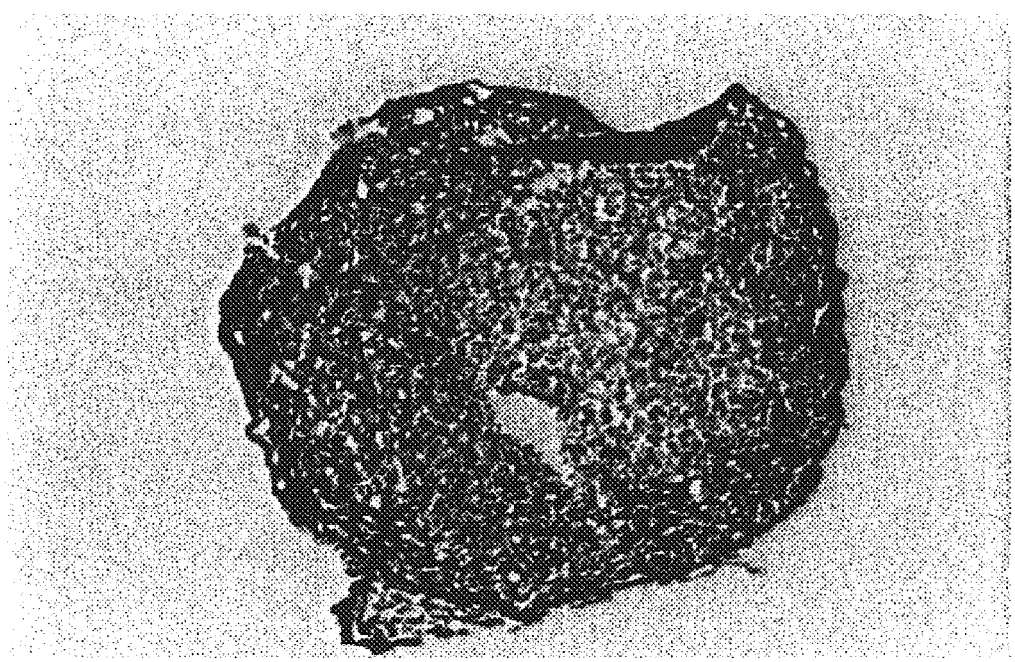
FIGS. 2A–2F show the in vitro chondrogenesis of human bone marrow-derived mesenchymal stem cells.
Figure 2B:
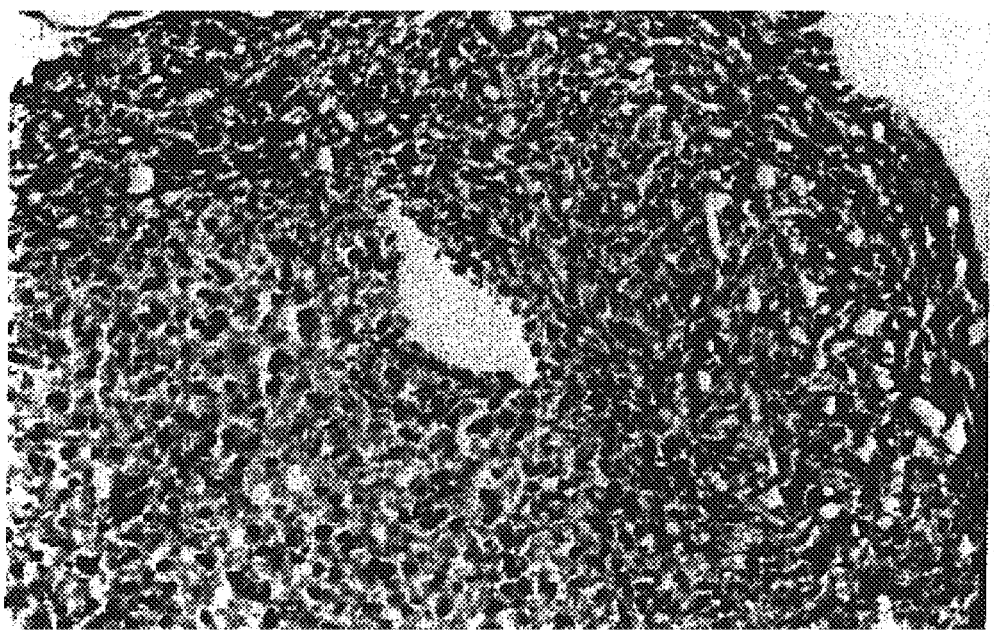
Figure 2C:
Figure 2D:
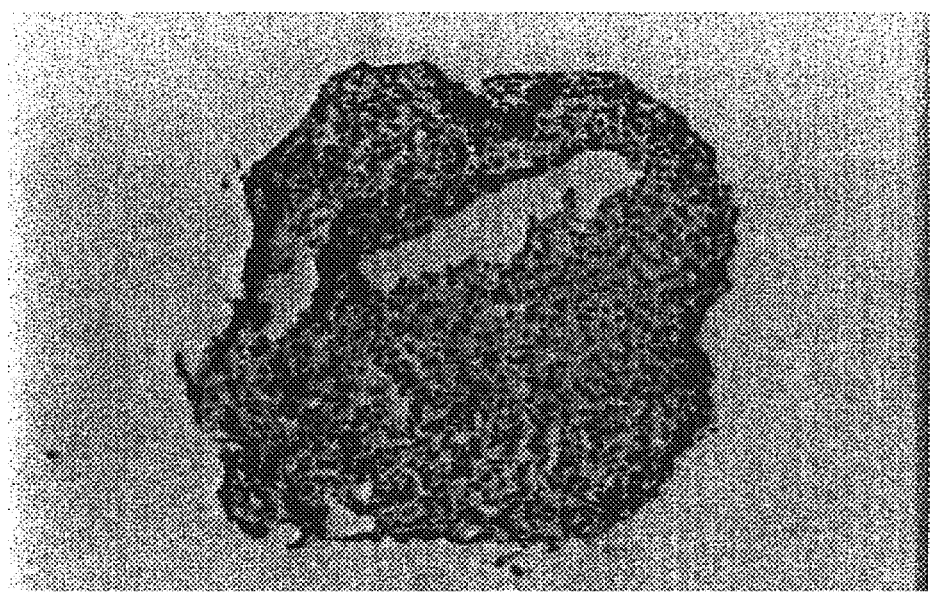
Figure 2E:
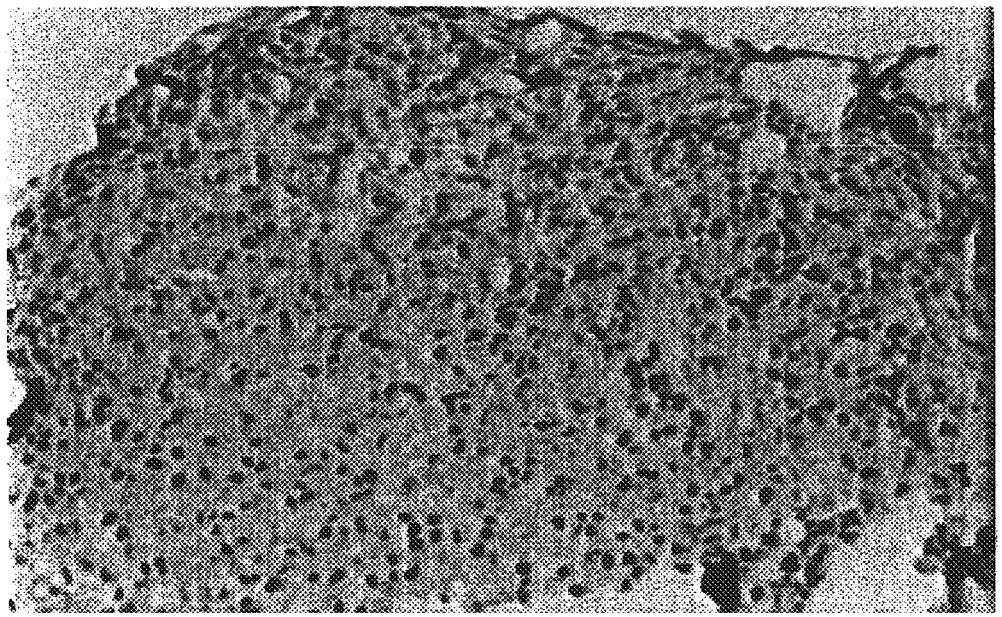
Figure 2F:
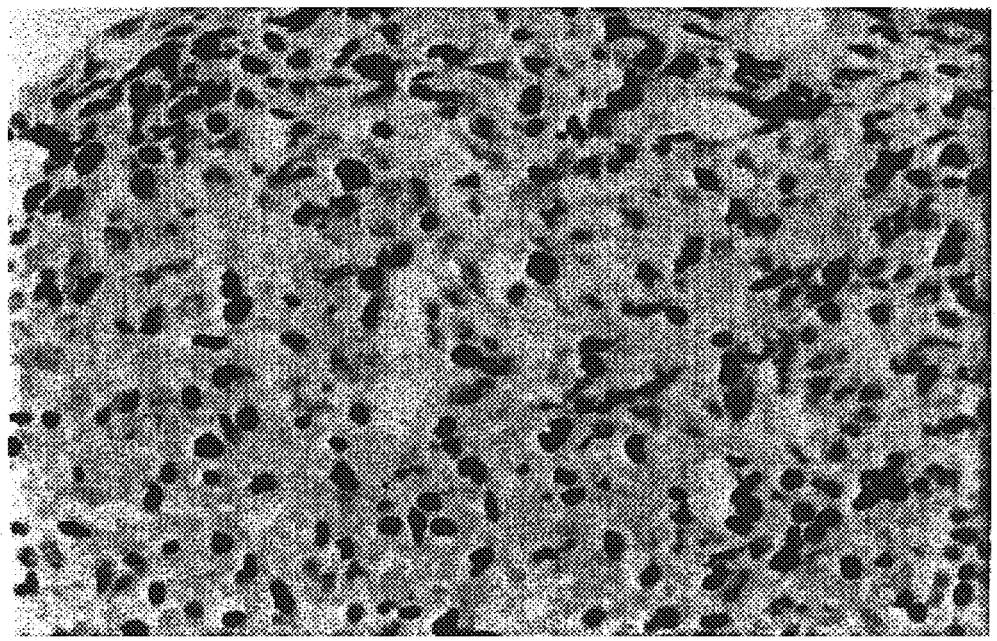

The implants of the present invention include a suspension of purified fibrillar collagen or modified collagen and culture-expanded human mesenchymal stem cells (hMSCs). These cells are the naturally occurring progenitors which give rise to multiple structural and connective tissues, including normal cartilage. The devices or implants of the invention, unlike preparations of cultured mature chondrocytes, have significantly more cartilage regeneration potential to restore hyaline cartilage which has degenerated at the site of a patient's osteoarthritic lesion(s). The ability to restore normal functional articular hyaline cartilage is due to the inclusion of cartilage progenitor cells.

Typically, a 10–20 cc marrow aspirate is harvested from the patient which yields 1,000–5,000 human mesenchymal stem cells. Approximately 10–50 million culture-expanded autologous human mesenchymal stem cells are then returned in the form of an implant. Most implants can be administered arthroscopically.

The implants of the invention are indicated for use in regenerating articular cartilage which has been lost through degenerative osteoarthritis. They are particularly suitable for treating patients with ongoing joint swelling, pain, stiffness and motion loss resulting from degenerative cartilage fissuring, pitting and erosions.

Implants containing autologous human mesenchymal stem cells are chondrogenic and, as such, regenerate hyaline cartilage directly at the graft site where they are able to differentiate into cartilage-forming chondrocytes. This process is referred to as "regenerative tissue therapy". The direct chondrogenic activity of human mesenchymal stem cells is superior to harvesting mature cartilage cells or other surgical techniques because human mesenchymal stem cells are able to recapitulate the original morphogenic (tissue-forming) events. Harvested chondrocytes are not able to replenish the pool of newly formed chondrocytes which have differentiated from mesenchymal progenitor cells.

Cartilage loss resulting from osteoarthritis cannot be regenerated via "harvested chondrocytes or "site-directed matrix implants" because these methods either cannot regenerate the normal pattern of cartilage extracellular matrix formation or they rely on the availability of suitable reserves of human mesenchymal stem cells in surrounding tissue to infiltrate the matrix implant. Patients over the age of 20–25 are generally unable to recruit or generate sufficient cartilage-forming progenitor cells to heal an osteoartitic lesion. By increasing the number of the patient's own mesenchymal progenitor cells and increasing the reservoir of available cartilage-forming progenitors, nominal cartilage can be restored, together with subchondral bone, using the body's own natural repair mechanism.

The implant is formed of a biodegradable matrix (biomatrix) which is combined aseptically with the culture-expanded autologous human mesenchymal stem cells at the time of surgery. The resulting mixture is then extruded through the mixing chamber either into the pre-drilled graft site directly, or into one of several other disposable implant molds. Within 10–15 minutes following mixing, the implant material (human mesenchymal stem cells and biomatrix) contracts, either within the implant site or for subsequent implantation in an arthroscopic or open procedure.

The rate at which the implant contracts may be varied by adding different amounts of contracting agent at the time human mesenchymal stem cells and biomatrix are combined. A slower contracting implant is easily administered by percutaneous methods such as traditional arthroscopy, fluorography-guided direct injection, or through the disposable implantation device provided by the invention.

Mesenchymal stem cells regenerate new cartilage and subchondral bone which conforms to the shape of the graft site. New cartilage and new subchondral bone is fully integrated with the surrounding mature host tissue and the collagen biomatrix components are eventually resorbed. Because the density of cartilage-forming units is uniform in the implant, the overall rate of new osteochondral tissue forms at similar rates regardless of the implant size.

Substantial new cartilage and bone is formed by 12–16 weeks after implantation, articular cartilage extracellular matrix continues to form and the subchondral bone remodeling process is already well underway. By 16 to 24 weeks, significant tissue morphogenesis has taken place, only traces of the biomatrix remain, and the neotissue is nearly indistinguishable from surrounding host tissue. The regenerated osteochondral tissue is thus incorporated into the patient's host cartilage and bone. Recapitulating the events of original endochondral tissue formation in the implant remodeling process ensures long-term structural integrity at the site of the previous osteoarthritic lesion. Only by starting with cartilage progenitor cells can the normal architecture of extracellular matrix molecules be formed.

The implants of the invention are prepared at the time of surgery using biomatrix material and the patient's own cells which have been previously harvested. The cells are culture-expanded for approximately 36 weeks after harvest, until 1–2 days prior to the scheduled regenerative tissue therapy surgery.

Mesenchymal Stem Cell Harvest and Culture Expansion

Using the bone marrow collection and transport kit (described below), a bone marrow aspirate from the medial posterior iliac crest is obtained by standard aseptic techniques in an out-patient procedure. A minimum sample size of 10–20 cc, which may vary depending on patient age, is required to assure an adequate concentration of human mesenchymal stem cells in the primary cultures. Since human mesenchymal stem cells decline with age, it is important to obtain the proper starting stem cell concentration.

Nucleated cells are harvested from the bone marrow and subsequently processed in individual batches under sterile tissue culture conditions which promote selective attachment of the rare mesenchymal stem cells. Typically, only 100 to 500 human mesenchymal stem cells per 10–50 million nucleated marrow cells (or fewer in the case of elderly patients) attach and grow in tissue culture. This translates to approximately 5,000 human mesenchymal stem cells per 10 cc marrow aspirate. The remainder of the cell population contains various types of non-adherent hematopoietic and stromal cells which are removed early in the cell culturing procedure.

Adherent marrow-derived human mesenchymal stem cells have homogeneous morphology, almost all being fibroblastic, with rare, polygonal cells. The adherent cells are seen as individual cells or small colonies of only a few cells on day 3; however, they replicate rapidly and form colonies of 50–200 cells within the first week of culture. By 10–14 days, the colonies of mesenchymal stem cells have expanded in size with each colony containing several hundred to several thousand cells.

To maintain mesenchymal stem cells in their undifferentiated state and to control their rate of replication, each primary human mesenchymal stem cell culture is passaged into new culture vessels when the culture becomes about 80–90% confluent. Cells in newly passaged cultures attach to form a uniformly distributed layer of cells which are 25–35% confluent at the time they are passaged. Cells continue to divide and are again passaged when cell density reaches about 80–90% confluence, yielding an average of 5 million cells per T-flask culture vessel.

The human mesenchymal stem cell preparations are preferably culture-expanded in a chemically-defined medium which does not require the addition of fetal calf serum or other serum supplements. This medium is the subject of co-pending, commonly assigned U.S. patent application Ser. No. 08/464,599 entitled "Chemically Defined Medium for Human Mesenchymal Stem Cells, filed Jun. 5, 1995.

Cells from each culture vessel can be replated many times without a loss in the osteochondrogenic potential of the cells. Therefore, a single primary culture starting with 100 to 500 adherent human mesenchymal stem cells can be expanded to well over one billion (10) cells. Typically, however, a small 10–20 cc marrow aspirate provides 25 primary culture vessels of up to 5 million cells, and consequently, sufficient cells for most implants can be obtained in fewer than 2–3 passages.

Regenerative Tissue Therapy Implant Procedure

The present invention is directed, inter alia, to the evolution of a regenerative tissue therapy using human mesenchymal stem cells to regenerate In addition to gels, the types of biomatrix materials that may be used include sponges, foams or porous fabrics that form a three-dimensional scaffold for the support of mesenchymal stem cells. These materials may be composed of collagen, gelatin, hyaluronan or derivatives thereof, or may consist of synthetic polymers, or may consist of composites of several different materials. cartilage lost due to osteoarthritis. This effort is aimed at developing a truly osteochondral therapy; that is, to create cartilage and subchondral bone tissue at critical sites rather than simply treating the symptoms of osteoarthritis. This approach to the problem is novel because it utilizes the replacement of the early progenitors of bone formation at the cellular level. However, the cell-based regeneration of bone will be designed to be effective in conjunction with diet, exercise, and other preventative therapies.

The implant preparation and regenerative tissue therapy of the invention are envisaged to improve significantly the quality of life for the osteoarthritic patient.

All procedures should be performed under standard aseptic conditions, following accepted guidelines for therapeutic arthroscopic procedures. The mesenchymal stem cells are maintained in a sterile liquid suspension at between 2° C. and 8° C. (36° F. and 46° F.) until the time of the implant procedure. All aspects of the human mesenchymal stem cell implant procedure should be performed in accordance with accepted standards for joint arthroscopy management.

Using the implant kit described herein, the premeasured biomatrix and contracting catalyst are combined with the autologous mesenchymal stem cells by gently passing them through the mixing chamber. Once mixing is complete, the viscous slurry of material may be extruded through the implant injector into the defect site using any one of the accepted delivery systems. After 10–15 minutes, the implant contracts and conforms to the shape or contours of the graft bed directly, or it can contract and be molded ex vivo. The implant is then removed, trimmed to fit the precise dimensions of the defect site, and implanted directly in the graft bed. Coverage of the implant and graft bed with soft tissue should then be achieved to complete the procedure.

The implants of the present invention are contraindicated (1) in sites with significant vascular impairment proximal to the implant site, (2) in the presence of systemic bone or cartilage disorders, (3) where substantial joint destabilization has occurred, including extensive osteophyte formation (4) where a substantial portion of the weight-bearing articular cartilage surface has eroded, (5) in an infected wound site, or (6) in femoral neck fractures or fractures of the epiphyseal plate.

Bone marrow collected with the bone marrow collection and transport kit described herein should be processed according to the protocol described herein.

Bone Marrow Collection and Transport Kit

Prep Tray: povidone iodine swab sticks (I % available iodine) (3); paper towel; fenestrated drape; and hospital drape.

Procedure Tray: Jamshidi bone marrow biopsy/aspiration needle, 4"; Illinois sternal/iliac aspiration needle, 15 GA;

bone marrow transport vessel, 20 cc; syringe (10 cc), Luer slip; syringe (20 cc), Luer slip; syringe (5 cc), with 20 GA×1½" needle; syringe (10 cc), Luer slip; 21 GA×1½" needle; 25 GA×⅝" needle; lidocaine hydrochloride USP, 1%, 5 ml (2); Heparin USP, 10,000 U/ml, 5 ml; scalpel blade with handle; gauze sponges (5); elastic bandage; probe; and plastic bags, (2);

Stem Cell Transport Container: protective wrap for transport vessel; plastic bag for ice; three (3) cold blocks; contents of unopened, undamaged package are sterile and nonpyrogenic.

Cartilage Implant Kit

The implant kit contains: biomatrix in premeasured sterile matrix container; human mesenchymal stem cells, preferably autologous, in premeasured sterile cell culture chamber or syringe (10 million, 25 million, 50 million human mesenchymal stem cells or custom implants); mixing chamber; arthroscopic graft site preparation instruments; and arthroscopic graft site implantation instruments; contents of unopened, undamaged packages are sterile and nonpyrogenic. Kits should be stored at refrigerated conditions between 20° C. and 80° C. (36° F. and 46° F.).

Regenerative therapy in accordance with the invention is envisaged to be useful in the presence of other symptomatic treatments, such as chronic analgesic or anti-inflammatory medicines. The numerous aspects of osteoarthritis therapy contemplated include those described in more detail below.

Regulation of Chondrogenesis

This aspect focuses on the identification of molecules regulating mesenchymal stem cells during chondrogenic differentiation, including factors controlling the development of articular hyaline cartilage. To regenerate hyaline cartilage in osteoarthritis patients under a variety of clinical scenarios, it is important to develop a better understanding of the molecules that control the chondrogenic lineage progression of human mesenchymal stem cells. In vitro, it has been possible to culture human mesenchymal stem cells as "pellets" or aggregates under conditions that promote chondrogenesis in serum-free, defined media. This system permits the screening of molecules for chondrogenic potential in vitro.

Molecules that regulate gene expression, such as transcription factors and protein kinases, are useful for monitoring chondrogenesis in vitro, and make it possible to demonstrate, for each batch of cells, that 1) the mesenchymal stem cells are maintained in an undifferentiated state and, 2) once committed, the mesenchymal stem cell-derived progeny cells are capable of progressing towards articular chondrocytes. Molecules that are secreted from the developing chondrocytes, such as extracellular matrix components and cytokines, are helpful in monitoring the chondrogenic process in vivo.

By way of background, molecules controlling chondrogenesis have been identified by several groups, and many are polypeptide growth factors of the BMP family, a sub-class of the TGF-β superfamily. However, the control of gene transcription that leads to chondrogenesis is not yet understood at the molecular level in part because there has not been a dynamic model system for chondrogenesis in vitro that accurately reflects the in vivo development of the tissue. More importantly, control of the phenotypic distinction between fibrocartilage and articular hyaline cartilage has not been understood.

Currently, investigators utilize model systems such as cultured articular chondrocytes, fibroblastic cell lines, and cultured fragments of cartilage in attempts to discover factors influencing chondrocyte formation, maintenance, and degradation. These models are best at showing the static profile of chondrocytes, that is, observing the expression of type II collagen and aggrecan molecules, for example, and screening factors that might up-regulate metalloproteinases or inappropriate collagens. However, the human mesenchymal stem cells represent a cellular model system that permits examining the dynamic commitment and differentiation of the cells down the chondrogenic lineage, replicating the events that occur during fetal development.

As an initial investigation the inventors have produced human mesenchymal stem cell pellet cultures that display reproducible chondrogenesis in vitro. FIG. 1 shows a cross section of such a pellet culture after three weeks in defined media. Several additional observations have been made to characterize these cultures. The basal media of the culture must contain sufficient sulfate and proline content to fuel the formation of sulfated proteoglycans and collagen, respectively. Ascorbic acid is also added to ensure proper collagen synthesis. Oxygen tension in the media is likely to be important to the selectivity and rate of differentiation, as chondrogenesis appears to be preferred at lower $PO_2$.

In further studies, several molecules have been identified that promote chondrogenesis in the mesenchymal stem cell pellet culture assay. The polypeptide growth factor, TGF-β3 causes more rapid induction of the phenotypic changes as defined by metachromatic staining with toluidine blue, morphology, and collagen H expression. TGF-β3 induces expression of type II collagen and link protein more rapidly than TGF-β1, and causes suppression of type I collagen. This suggests that TGF-β3 might be useful to accelerate chondrogenesis in vivo in an implant, or to help mesenchymal stem cells commit quickly to the chondrocyte lineage in the manufacturing culture system, prior to implantation.

Several cytokines have been implicated in the degradation of the extra-cellular matrix and the suppression of the chondrocytic phenotype expressed by articular chondrocytes in culture. In particular, IL-1 (7), IL6, and TNF-α (8) appear to enhance the degradation of cartilage matrix by up regulating expression of metalloproteases with specificity for aggrecan and type R collagen. They also suppress the expression of type H collagen, aggrecan, and other proteoglycans (10). Other cytokines, such as IL4 and IL-10, appear to have a chondroprotective effect (11). Therefore, it is of interest to understand the effects of cytokines, such as IL-1, on human mesenchymal stem cells. Using immunochemical assays for proteins and PCR-based assays for mRNA, the inventors have established that mesenchymal stem cells produce several cytokines constitutively, including M-CSF and stem cell factor (SCF, also known as c-kit ligand).

In response to IL-1α or β, the mesenchymal stem cells produce a variety of hematopoietic cytokines, such as G-CSF, GM-CSF, IL6, IL-11, among others. This has been interpreted to reflect the differentiation of the mesenchymal stem cells down the lineage of bone marrow stromal fibroblasts, the cells that form the microenvironment in the marrow for hematopoiesis. In addition, IL-1 treatment dramatically up-regulates the production of the IL-1 itself from human mesenchymal stem cells. Thus, IL-1 treatment appears to be detrimental to the chondrogenesis of human mesenchymal stem cells. This suggests that inhibitors of IL-1 function and suppression of inflammatory reactions would be important parameters to control in mesenchymal stem cell-directed cartilage regeneration.

Cellular and Molecular Assays in Osteoarthritis

In this aspect, development of quantitative assays for the progression of osteoarthritis (OA) using mesenchymal stem cells and proprietary reagents and advanced biochemical methods are employed to measure the number and distribution of mesenchymal stem cells and molecular markers from OA patient and animal models of OA. Assays are used as outcome measures for the work in vitro as well as in vivo in animals and humans. The assay measurements provide information as to the state of the extracellular matrix, as well as the cells and cytokines present during OA. The mesenchymal stem cell-based regenerative therapy not only restores functional joints, but also reverses the abnormal levels of the various degenerative markers in the assays. The measurements are preferably made on cultured cells and their products, such as conditioned media in vitro, and from samples of synovial fluid, in vivo.

The synovium represents the most accessible source of material in vivo, although it is possible that other physiological fluids (blood, plasma, serum, urine, or lymph) could provide useful information on more systemic factors. The assays cover: 1) the cellular environment, that is, the phenotype of cells present at the time of testing; 2) the endocrine environment, that is, the cytokines, hormones, and other soluble factors present; and 3) the matrix environment, that is, the materials comprising the insoluble, extracellular compartment, and their by-products. Analysis by NMR and other imaging techniques provides additional information on the joint under examination, as well as gait analysis or other appropriate physical testing.

Some of the factors that signal between the cells in the joint, for example certain cytokines, (specifically IL-1 and TNF-$\alpha$), have deleterious effects on cartilage by: 1) suppressing collagen H synthesis while stimulating collagen I production (7); 2) inducing metalloproteases, such as collagenase-3, and blocking protease inhibitors (e.g. TIMP-1) (20); 3) activating aggrecan breakdown including keratan sulfate release; and 4) inducing other cytokines that support hematopoietic differentiation, such as IL-6, possibly promoting the production of neutrophils, macrophages and other cells harmful to cartilage.

Other soluble growth factors, including IGF-I (21) and TGF-$\beta$1 (22) have been found to have the opposite effects from IL-1 in cultured articular chondrocytes, and may be able to block the actions of IL-1. There are valid approaches to therapeutics in OA based upon this information. For example, inhibition of IL-1 with the IL-1 receptor antagonist protein could, temporarily, alleviate symptoms due to the action of IL-1, but would not be long-term unless provided as gene therapy.

Inhibitors of metalloproteases is another promising avenue of drug development to arrest the degeneration of cartilage matrix, but will not produce new chondrogenesis at the OA joint. mesenchymal stem cell-based regenerative tissue therapy could supplement other modes of treatment. It is of critical importance to understand the cellular, hormonal, and matrix environment that mesenchymal stem cells will encounter in the OA joint.

Specific reagents and procedures are in place to characterize mesenchymal stem cells from bone marrow aspirates, including a panel of monoclonal antibodies and defined culture conditions that promote mesenchymal stem cell growth. Therefore, it is immediately possible to characterize the numbers and characteristics of the mesenchymal stem cells obtained from bone marrow aspirates (approx. 5–10 ml) of OA patients. This analysis is important to understanding if there are any difficulties in isolating or identifying the mesenchymal stem cells of OA patients.

Marrow samples of over 300 donors have been processed by the inventors and all gave viable mesenchymal stem cell cultures. While complete clinical histories are not available on all samples, several of these patients were known to have osteoarthritis, and many others were elderly (7th to 9th decade) and were very likely to have some degenerative joint disease. Thus, it is unlikely that the presence of mesenchymal stem cells in bone marrow is a limiting problem. Further characterization of the cellular environment for mesenchymal stem cells in OA is focused on synovial fibroblasts and the possible presence of macrophages and neutrophils in the synovial fluid and/or cartilaginous tissue. The extracellular matrix environment is currently being probed using antibodies and other reagents generously provided by D. Heinegard (Lund, Sweden) and B. Caterson (Cardiff, U.K.).

Work is continuing on this aspect in our analytical biochemistry laboratory, designed specifically for the analysis of protein and carbohydrate moieties of the proteoglycans of the extracellular matrix. This includes high performance liquid chromatography (HPLC), capillary electrophoresis (CE), protein sequencing, amino acid analysis, carbohydrate compositional analysis, mass spectrometry (MS), and analysis of peptides by matrix-assisted, laser-desorption, time-of-flight, mass spectrometry (MALDI-TOF).

The methods under development bring on-line MS and HPLC to the analysis of matrix molecules. Previously, these advanced biophysical and biochemical methods have not been utilized extensively in the field of OA. Comprehensive analysis of these molecules is a key to 1) elaborating the molecular and cellular etiology of OA, and 2) reconfirming that mesenchymal stem cells can restore normal hyaline extracellular matrix architecture by recapitulating the sequence of embryonic cartilage formation.

These studies assess the mesenchymal stem cells, synoviocytes, and monocytes/macrophages present in relevant tissues of OA patients compared to age matched, normal controls. Patients with diagnosed OA at early, middle, and late stages provide marrow aspirates from the iliac crest and samples of synovial fluid of the knee joint, as well as peripheral blood. In cases where patients are undergoing total joint replacement, long bone marrow (e.g. femoral head or knee) and cartilage biopsy explants are collected as well. The tissue is dissociated to a mononuclear cell fraction and, from this, quantitation of various cell types is performed by flow cytometry.

Further fractionated cell populations are cultured under various conditions to obtain mesenchymal stem cells (SH2 antibody positive), synovial fibroblasts, and monocytes/macrophages (CD45 positive). Colony counts from each population and antibody reactivity are used for further characterization of the cell preparations. In cases where articular chondrocytes can be obtained from biopsied cartilage, cells are subjected to a panel of PCR and antibody-based assays using, for example, the ILA marker of chondrocyte de-differentiation (Schwarz et al., 1993).

Synovial fluid and serum from OA patients, cleared of cells by centrifugation, are subjected to a battery of immunoassays for cytokines, hormones, and other growth factors. Among the molecules of particular interest are: IL-1 ($\alpha$ and $\beta$), IL-6, TNF-A, TGF-0 (1,2, and 3), PTH, IGF-1, and thyroid hormones (T3 and T4). Preferably high throughput robotic systems are used.

Synovial fluid and serum samples are screened from OA and aged-matched normal controls for matrix markers that are indicative of OA. Matrix markers from serum include: COW and BSP as has been documented by Heinegard and coworkers (16) and keratan sulfate (KS) as has been shown by Thonar and coworkers (32). The same markers as well as collagen and other matrix proteins are also measured in synovial fluid. Synovial fluid markers include the C-propeptide of collagen II, as well as other collagen II fragments, collagenase, and other metalloprotease activity. Aggrecan G3 domain is a useful marker for matrix degradation, particularly when measured coordinately with the aggrecan G1 domain and the related Link protein (15). Using MALDI-TOF mass spectrometry, the extent of post-translational modifications of molecules such as aggrecan G1 domain can be measured. This type of analysis is described in more detail below. Peptide maps by HPLC, mass spectrometry and partial sequence analysis are utilized to establish the identity of the protein fragments and to validate the assays. These measurements provide a clear indication of the diagnostic stages of cartilage matrix degradation.

The biochemical and cellular markers are correlated with the clinical diagnosis and other parameters, as available, including high resolution NMR images; radiographic imaging, and composition of biopsy cartilage tissue. These techniques give useful information on the thickness of the joint cartilage, the joint space per se and, in cases of joint removal, biochemistry of the diseased tissue itself.

Mass Spectrometry of Osteoarthritic Cartilage Components

Aggrecan, the major aggregating proteoglycan of cartilage, is degraded by proteolytic enzymes as part of the remodeling process. In osteoarthritis, aggrecan degradation occurs in an uncontrolled fashion, resulting in breakdown of the cartilage integrity. While aggrecan structure has been studied, changes between the normal and diseased states are not known in detail. Of particular interest are changes in the extent of glycosylation which may increase aggrecan proteolytic susceptibility. In order to define an aggrecan phenotype typical of osteoarthritic cartilage, a statistically significant number of patients should be studied. A technique capable of generating data rapidly that provides detailed information on the aggrecan structure from small quantities of tissue would be useful for this purpose. Traditional western blotting techniques, while rapid, do not provide structural detail. Edman sequencing provides some structural detail but cannot measure the size of carbohydrate and is too slow to be accomplished on multiple tissues. The inventors have found that mass spectrometry is rapid and provides a great deal of structural detail.

MALDI-TOF analysis required sample treatment in guanidine hydrochloride. GuHCl, commonly regarded in the mass spectrometric community as a contaminant, is usually removed before protein analysis. However, we found that the denaturant enabled the analysis by breaking down noncovalent aggregates of the sample molecules, as cartilage components tend to aggregate.

Cartilage was extracted with guanidine hydrochloride, dialyzed, fractionated by associative and dissociative cesium chloride density centrifugation and the aggrecan G1 domain was isolated by chromatography. MALDI-TOF mass spectrometry was then used to profile the heterogeneity of the aggrecan molecule and to measure the extent of glycosylation. MALDI-TOF involved diluting the sample in a matrix solution, usually sinapinic acid for large proteins.

Isolated aggrecan G1 domain was reduced and alkylated, and digested with trypsin. The tryptic digest was separated chromatographically. The digest for a control tissue was thoroughly characterized using a combination of mass spectrometry and Edman sequencing with respect to position and extent of post-translational modification and with respect to the C-terminus. Experimental tissues were screened by liquid chromatography-mass spectrometry for changes occurring with respect to the control tissue.

Figure 3A:
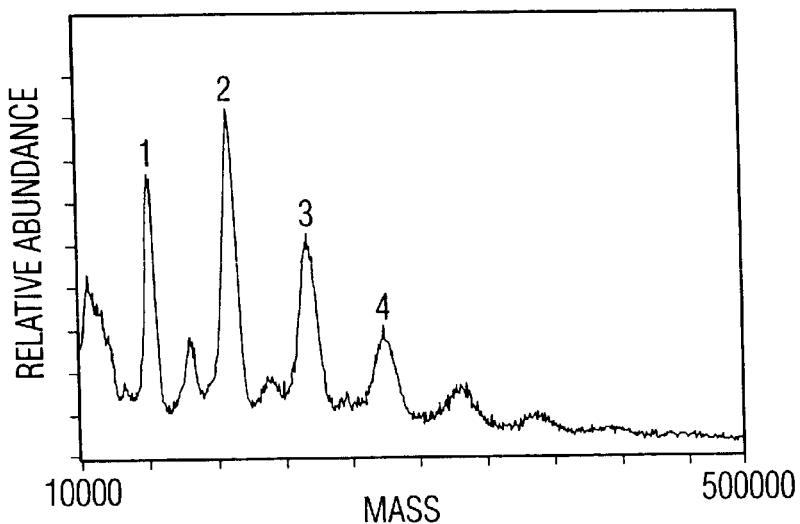
FIGS. 3A–3C show an analysis of aggrecan G1 domain by MALDI-TOF.

The results of the analysis of pig aggrecan are shown in FIG. 3A. The peak labeled 1 corresponds to monomeric pig aggrecan G1 domain. Peaks 2, 3 and 4 correspond to the dimer, trimer, and tetramer, respectively, of the molecule. For any protein to show such a pattern was extremely unusual and illustrated the propensity of aggrecan G1 domain to aggregate in solution.

When a human aggrecan G1-containing fraction isolated by AID4 density centrifugation was run under the same MALDI-TOF mass spectrometric conditions, no ion signal was obtained. A series of tests showed that G1 concentration should have been sufficient to produce data and that no chemical contaminants interfered with the ionization process. When the sample was mixed with the denaturant guanidine hydrochloride to produce a 4M solution before mixing with sinapinic acid solution, ion signal was obtained, indicating that no aggregates formed.

Figure 3B:
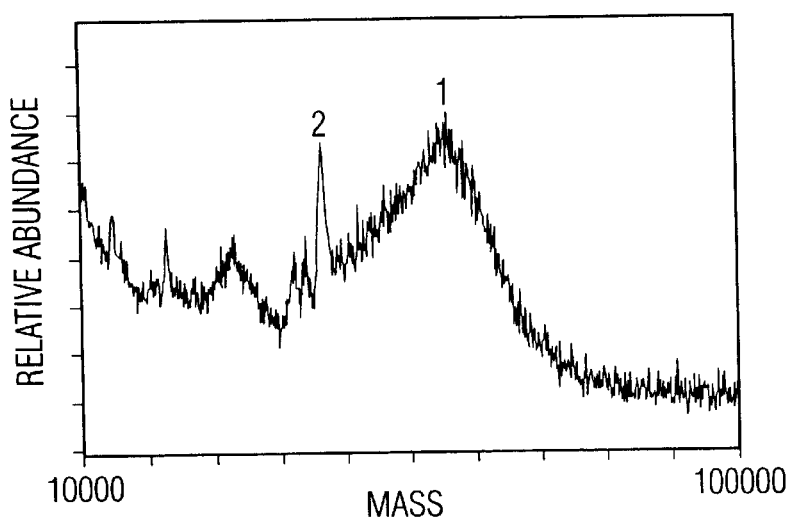

FIG. 3B shows the spectrum obtained for an aggrecan G1 isolated from human osteoarthritic tissue. The peak labeled 1 corresponds to human aggrecan G1 fragment generated in the cartilage tissue in vivo. The breadth of this peak is substantially greater relative to that observed in FIG. 3A for the pig aggrecan G1 and provides a measure of molecular heterogeneity. The sharper peak labeled 2 corresponds to link protein.

Figure 3C:
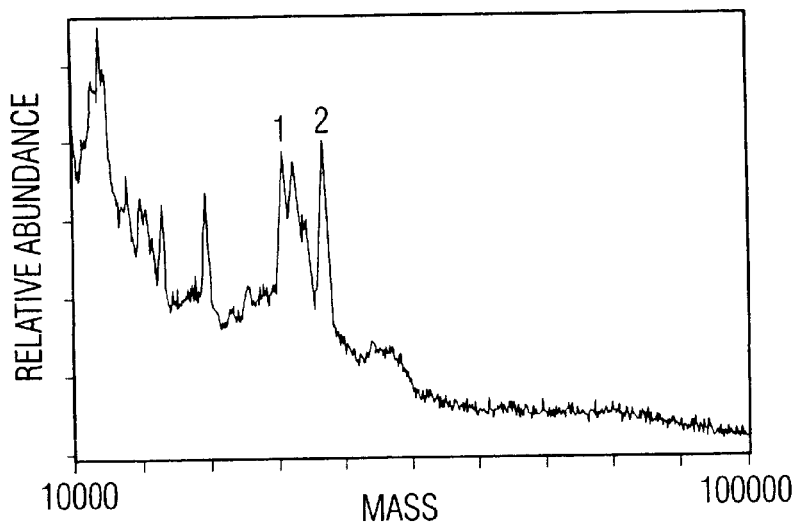

FIG. 3C shows human aggrecan G1 after reduction and carboxymethylation. The peak labeled 1 corresponds to aggrecan G1 after removal of keratan sulfate chains. The peak labeled 2 corresponds to link protein. The peaks between 1 and 2 are believed to be link variants, also observed in FIG. 3B.

These data show that the extent of post-translational modification of aggrecan G1 domain can be measured using MALDI-TOF mass spectrometry. The data can be acquired rapidly to build a database, and provide a useful means to compare cartilage samples collected from a large patient pool.

Preclinical Models of Osteoarthritis

Many of the various animal models of osteoarthritis center on the surgical destabilization of the knee, followed by a waiting period of weeks to months during which time, the articular surface of the femoral condyle becomes pitted and eventually eroded in a manner reminiscent of that of clinical OA (35). These models revolve around alteration of the knee joint forces by transection of the anterior cruciate ligament, partial meniscectomy, or total patellectomy. Other models of OA can arise from immobilization with or without compression, and from altered forces applied to the joint. In addition, there are spontaneous mutant rodent models that arise from abnormal collagen crosslinking in the cartilage matrix. While this may reflect the pathophysiology of certain human inherited forms of OA involving collagen II mutations (36), it is not clear how well these spontaneous models reflect human OA arising from aging and osteochondral injury. The consensus of the February 1996 Orthopaedic Research Society workshop on "Surrogate Approaches to Experimental Modeling of Human Osteoarthritis" was that the canine ACL disruption model is the most useful system available at the present time to evaluate therapeutic approaches to OA.

The canine ACL-resection model (Pond-Nuki) (33) is the preferred system because besides human mesenchymal stem cells, the canine mesenchymal stem cells have been the best characterized preparations of the cells, and because canine has been the standard model system used for other mesenchymal stem cells-based products. Canine models are also standards of practice in experimental orthopaedics. As an alternative, the rabbit model developed by Moskowitz and coworkers (34) can be used. Rabbits are smaller and less expensive than dogs, allowing for larger numbers of experimental procedures. However, the biomechanical forces in the rabbit knee are quite different from the canine and human situation, and while freely mobile, the rabbits have restricted room for motion.

The canine model of OA, introduced in 1973 by Pond and Nuki (33), develops ten weeks following transection of the anterior cruciate ligament (ACL) of one knee (stifle) joint by means of lateral arthrotomy. The contralateral side can be used as a control although not ideal because any systemic endocrine changes could affect both sides, and compensatory mechanical forces may alter the joint space of the control side differently than would sham operated control animals. At early times following surgery, the amount of collagen II and aggrecan protein and mRNA appear to increase dramatically, as if a repair attempt was in progress (37, 38). At present, the canine ACL (Pond-Nuki) model appears to be the industry standard for OA therapeutics.

The rabbit model of OA (34) employs resection of approximately 30% of the anterior aspect of the media meniscus. Within several weeks after meniscectomy, deterioration of the cartilage is evident from physical lesions, such as pits, ulcers, fissures and cysts, as well as from decreased matrix proteoglycan content. Studies of the metabolic consequences of partial meniscectomy reveal that at early times following surgery there is increased cell proliferation, proteoglycan production and protein synthesis. However, the long-term effects of this procedure appear to be degenerative, ultimately resulting in loss of cellularity and matrix proteoglycan and increased osteophyte formation. The partial meniscectomy model is representative of the degeneration seen clinically following meniscal injury. Considerable information can be garnered from the repair of focal lesions to the articular cartilage. Repair of focal full-thickness defects of the articular cartilage and subchondral bone appears to depend on the age of the animal and the size of the defect. Above a critical size of approximately 3 mm in the adult rabbit, healing does not occur, while in 1–2 mm lesions significant repair can occur in the adult and at a higher rate in skeletally immature animals in which the endochondral growth plate is not yet closed.

Mesenchymal stem cells have been used to regenerate articular cartilage in rabbits, demonstrating the chondrogenic potential of the cells in vivo (19). The rabbit osteochondral defect model has been extended to canine articular cartilage of the knee, and provides the basis for the in vivo chondrogenesis work in our laboratories. Preclinical studies are in progress for autologous mesenchymal stem cell therapy for focal defects to the articular cartilage in both rabbits and dogs.

The gel formulation of the implant of the invention is tested using skeletally mature, male dogs (>14 months of age, >30 kg). Prior to surgery, the animals will undergo marrow aspirates from iliac crest, and autologous canine mesenchymal stem cells (cMSCs) are cultured. In the model procedure the anterior cruciate ligament is transected by lateral arthrotomy, and a separate cohort is sham operated. As noted above, the contralateral side can be used as another control. Based on time course data from the rabbit studies, implants are made arthroscopically into one or more lesion sites on the articular surface. While the canine model is different from the rabbit meniscectomy, this gel formulation is most effective early in the progression of the pathology.

Implant Device & Composition Embodiments

The implant, device and/or composition of the invention utilizes autologous mesenchymal stem cells in a gel, liquid or molded configuration to regenerate the articular, hyaline cartilage via the developmental course seen during embryonic differentiation. This is fundamentally distinct from other cellular therapies because it harnesses the capacity of the earliest progenitor cells to form the multilayer tissue that has been eroded by disease. Three principal embodiments of implants, devices and compositions containing mesenchymal stem cells have been developed in accordance with the invention.

The first embodiment is a gel suspension of mesenchymal stem cells in bovine, acid processed Type I collagen. Chemically cross-linked collagen can be manipulated quite easily and allowed to "gel in place" following arthroscopic injection of the liquid components. All matrix materials used are resorbable over a period of several months. The gel materials include collagen gel alone, cross-linked collagen gel, fibrin glues and alternative formulations, including autologous fibrin gels.

As the pathology of OA advances, the pits, lesions and fissures in the articular surface give rise to larger areas devoid of cartilage where increased bone formation can occur in the form of osteophytes and at latter stages, as bone fill of the joint space. Gel formulations that are optimized to fill lesions of "critical" size (24 mm) may not be adequate to address more advanced osteoarthritic joints.

The second formulation is a liquid suspension of autologous mesenchymal stem cells either in autologous serum or buffered saline that can be introduced directly into the synovial cavity. The mesenchymal stem cells in the liquid suspension home directly towards the sites of lesions on the articular surface. High doses (>$10^8$ cells) of mesenchymal stem cells can be infused without clumping and without ectopic tissue formation.

For the late stages of OA, when patients are approaching a total joint replacement, a third formulation, in accordance with the invention, is in a moldable gel format so that orthopaedic surgeons can apply it directly to the affected surface in an open procedure. Separate studies of tendon regeneration have developed a method for the preparation of a thick collagen gel suspension of mesenchymal stem cells that has been contracted onto a suture under axial tension. This preparation has been shown to be a mechanical and biologically stable repair material for tendon. A version of this can be applied to the third embodiment for a molded articular cartilage configuration.

IL-1 should be suppressed at the site of introduction of the mesenchymal stem cells, if cartilage is the desired result. Collagenases and other degradative enzymes should also be blocked to allow proper production of matrix material by the mesenchymal stem cells. Thus, compounds that inhibit IL-1 (e.g. IRAP) and/or metalloproteinases (e.g. Tenidap) should be administered.

Some preparation of the articular surface may be necessary via arthroscopic surgery, such as debriding the surface of the lesions and, perhaps, coating with a material suitable for the attachment of mesenchymal stem cells in vivo, such as fibronectin. The concept of this formulation is to allow the mesenchymal stem cells to move directly to the surfaces that require their action. In addition, the mesenchymal stem cells may need to be previously committed to the chondrogenic lineage so that they do not form additional bone on the exposed subchondral surfaces.

A particularly preferred embodiment is the molded gel matrix for resurfacing the entire condyle in advanced OA. This is a molded gel containing mesenchymal stem cells, which is positioned on a structural support, such as a woven sheet of suture material. An extension of this embodiment is a suture or other fibrous network, either pressed or woven, on which is impregnated and contracted a gel suspension of mesenchymal stem cells. The implant is molded to the shape of the affected condylar surface, and held in place by suturing it to the periosteum or other mechanical means. Alternatively, another material such as autologous fibrin glue can be used to hold the molded material in place.

EXAMPLE 1

MSCs derived from human bone marrow were cultured in DMEM (low glucose) with 10% fetal bovine serum until confluent, detached by trypsinization and transferred to minimal culture medium without FBS but with 10 M dexamethasone and ascorbic acid-2-phosphate. The cells ($0.2 \times 10^6$) were spun at low speed and maintained in the presence of dexamethasone and TGFβ-3 (10 ng/ml). After 2 days the cells formed a pellet about 1 mm in diameter. They were maintained for 21 days and then stained for the presence of type II collagen using monoclonal antibody C4F6. In the presence of TGFβ-3 the pellets were larger due to the fact that the cells produced more extracellular matrix and the differentiation process resulting in the formation of hypertrophic cells with well-developed pericellular matrix and expanded interterritorial matrix. This phenotype more resembles that of articular cartilage. FIGS. 1A to 1F illustrate cross sections of stained pellets.

EXAMPLE 2

Cells were isolated from human bone marrow as described and were cultured under the conditions as described in Example 1 but without the addition of TGFβ-3. After 21 days cells were stained with an anti-collagen II polyclonal antibody (Rockland). Under these conditions the cells developed a chondrogenic phenotype and synthesized and secreted collagen type II, as well as other cartilage markers such as link protein, keratan sulfate and COMP (cartilage oligomeric matrix protein). In rabbit cells treated under the same conditions, the chondrogenic phenotype also developed, but in a host-dependent manner. FIGS. 2A–2F illustrate cross sections of stained pellets.

EXAMPLE 3

The cartilage regeneration described in this example is directed toward the repair of focal full-thickness lesions in relatively young adults, generally resulting from sports-related or traumatic injuries. The ultimate goal of the product development program is to regenerate articular cartilage destroyed by osteoarthritis. Articular cartilage has a limited reparative capacity. Full thickness injuries that penetrate the subchondral bone undergo repair by a variety of mechanisms that generally fail to produce hyaline cartilage at the articular surface. In rabbits, repair of such lesions generally leads to fibrocartilaginous tissue. This generally progresses to fibrillated tissue after 6 months (Shapiro et al., 1993).

Mesenchymal Stem Cell (MSC) based repair of osteochondral lesions has been investigated in a series of implant studies carried out at both Case Western Reserve University and the inventors in a standardized osteochondral defect model in the rabbit knee.

Procedures used generally follow the methods described by Wakitani et al. (1994). Adherent cells derived from tibia bone marrow aspirates were cultured by standardized procedures and implanted at the end of first passage. Full-thickness defects (6 mm long, 3 mm wide and 3 mm deep) were made on the weight bearing surface of the medial femoral condyle by drilling 2 adjacent holes and curetting the bridge between them.

MSCs were mixed with acid-soluble type I collagen and gelled prior to implantation. The cell-collagen gel was partially dehydrated and manually transferred to the prepared defect. Control defects were left unfilled (i.e., no cells and no vehicle).

Animals were sacrificed at 4 weeks and the femoral condyles were formalin-fixed, embedded in paraffin using standard methods and sectioned for histology. Serial sections were stained with toluidine blue and by immunocytochemical methods with antibodies to cartilage extracellular matrix markers.

For determining MSC distribution in defects, cells were labeled by incubation with the membrane-binding dye Dil (Molecular Probes) overnight, mixed with carrier autologous collagen gel, partially dehydrated and implanted into defects of 3 mm diameter. Control defects were left unfilled. Sections of approximately 1 mm were cut from the center of the defect, exposed to full spectrum light on a fluorescence microscope and photographed.

Figure 4A:
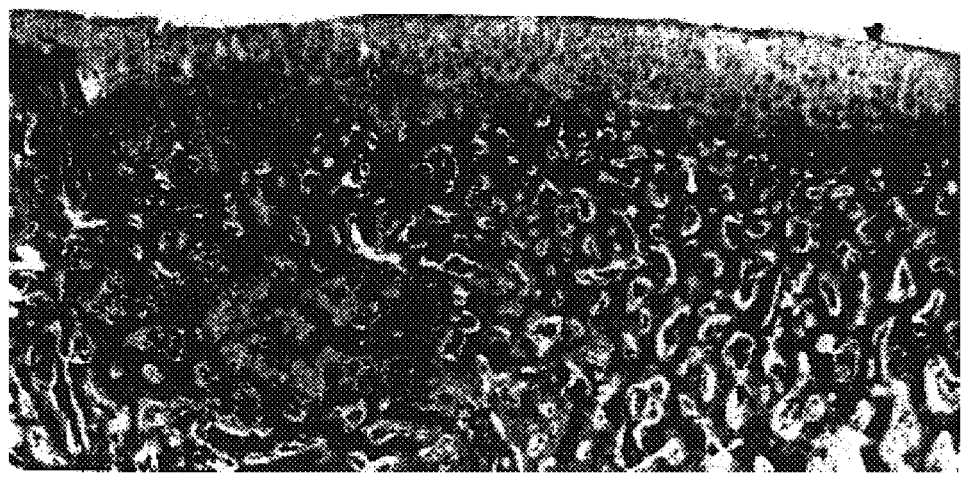
FIGS. 4A–4G show serial sections of an MSC implant after 4 weeks.
Figure 4B:
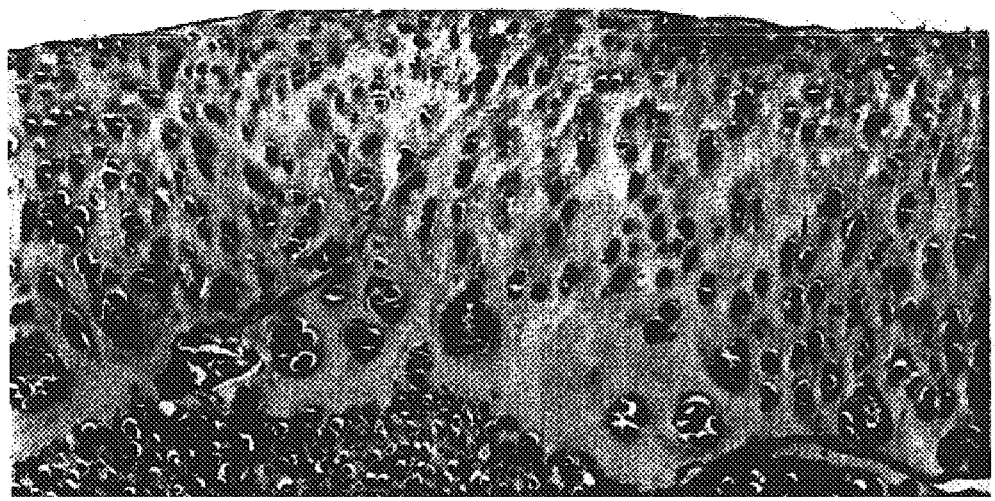
Figure 4C:
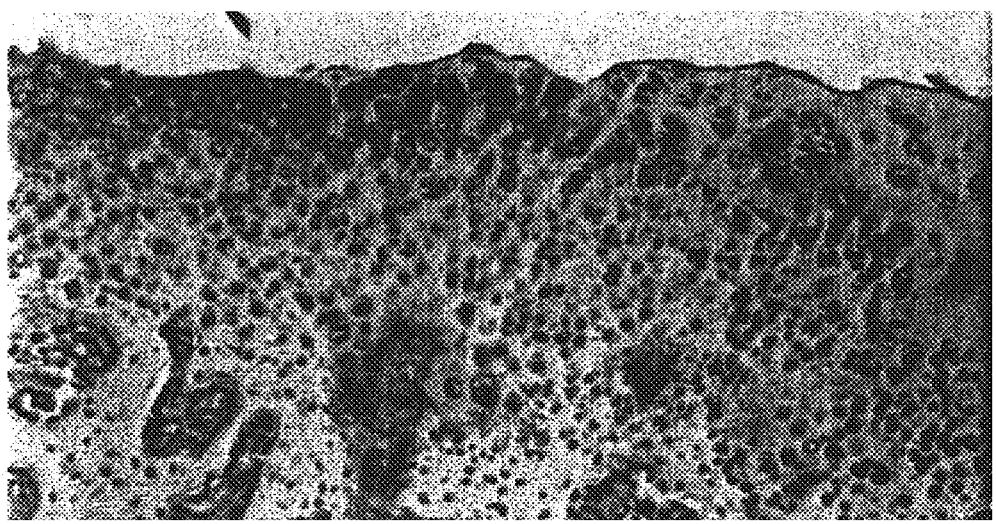
Figure 4D:
Figure 4E:
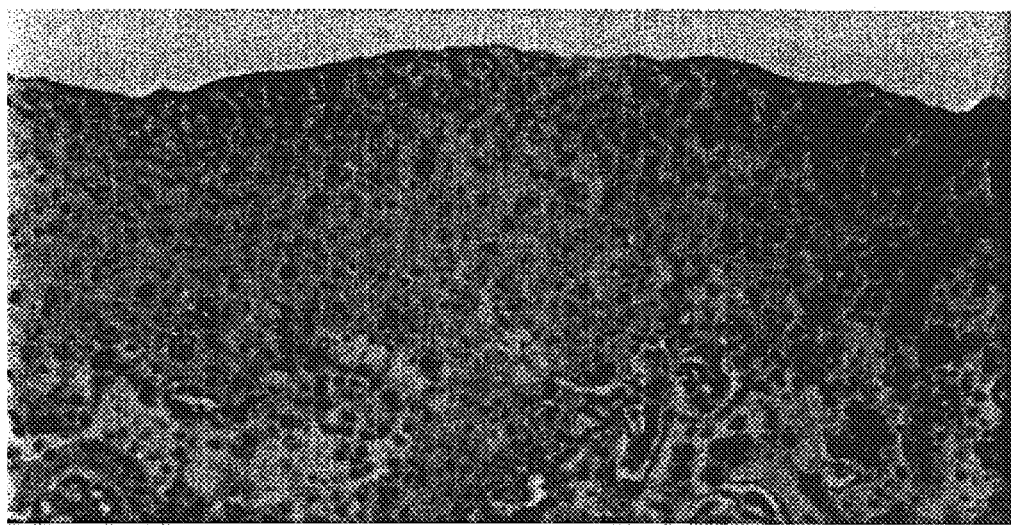
Figure 4F:
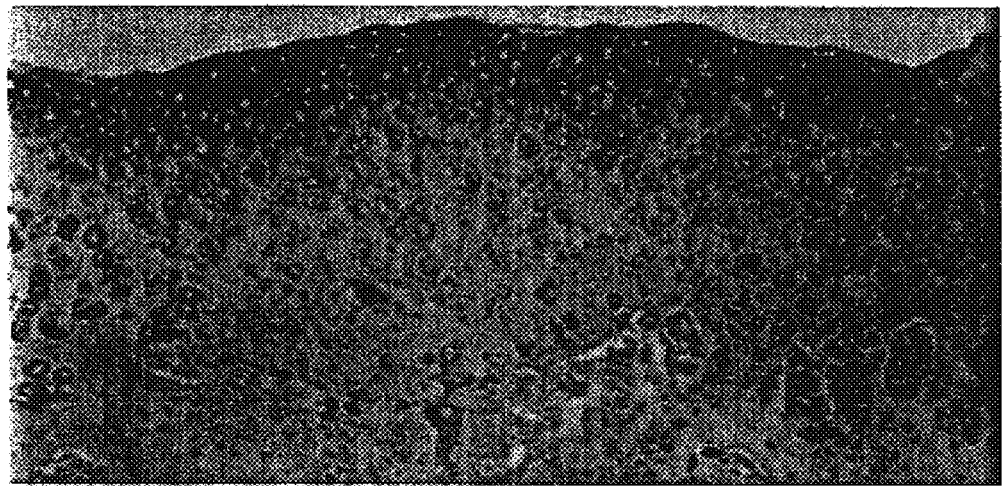
Figure 4G:

An example of autogolous MSC-mediated articular cartilage repair 4 weeks after implantation is illustrated in FIG. 4A, stained with toluidine blue. FIGS. 4B–4G show serial sections of the same repair tissue at higher magnification.

Formation of the tideline at the appropriate level is almost complete.

Initial formation of columns of chondrocytes is evident.

Regeneration of subchondral bone is almost complete.

A range of matrix markers, reflecting those found during development of normal cartilage, is expressed in the regenerating articular cartilage.

Figure 5A:
FIGS. 5A–5B show (a) control tissue without cells or matrix carrier both stained with toluidine blue.
Figure 5B:

FIGS. 5A and 5B show control tissue (i.e. empty defects which received no cells and no matrix).

Subchondral regeneration is generally incomplete in control defects.

A fibrous layer is formed in most control defects.

Figure 6A:
FIGS. 6A–6B show DiI-labeled cells in a standard 3 mm defect 6 days post-implantation.
Figure 6B:
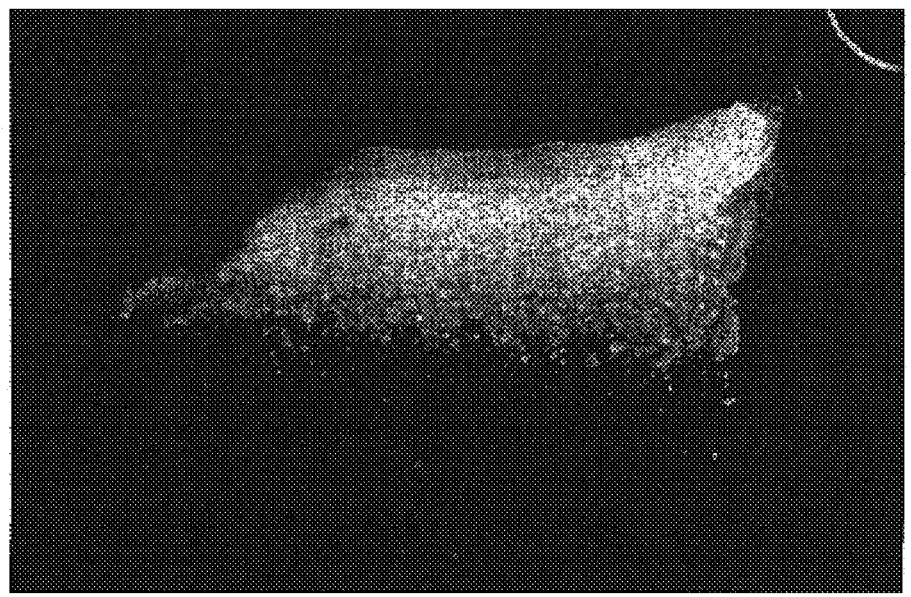

FIGS. 6A and 6B illustrate the distribution of Dil-labeled MSCs 6 days post-implantation.

Labeled cells are distributed throughout the defect.

Cited Literature

1. Johnston, B., Yoo, J., Barry, F. P. *Trans. Orth. Res.,* 42: 65, 1996.
2. Seyedin, S. M., Thomas, T. C., Thompson, A. Y., Rosen, D. N., Piez, K. A.: Purification and characterization of two cartilage-inducing factors from bovine demineralized bone. *Proc. Natl Acad. Sci. USA* 82:2267, 1985.
3. Silbermarm, M., Iwamoto, M., Kato, Y., Suzuki, F.: TGF beta stimulates DNA synthesis in precartilage cells but depresses alkaline phosphatase activity in chondrocytes and the calcification of the cartilage extracellular matrix in vitro. *Calcif Tissue Inc.* 42(Suppl.) A25, 1988.
4. Stam, K., Steward, A. A., Qu, G. Y., Iwata, K. K., Fenyo, D., Chait, B. T., Marshak, D. R., Haley, J. D.: Physical and biological characterization of a growth inhibitory activity purified from the neuroepithelioma cell line A673. *Biochem. J.* 305:87–92, 1995.
5. Stewart, A. A., Haley, J. D., Qu, Guo Y., Stam K, Fenyo, D., Chait, B. T., Marshak, D. R., Ng, A., Yuk-Kiu, Marley, G., Iwata, KK: Umbilical cord transforming growth factor-B3: isolation, comparison with recombinant TGF-B3 and cellular localization. submitted for publication.
6. Amar, S., Sires, B., Sabsay, B., Clohisy, J., Veis, A.: The isolation and partial characterization of a rat incisor dentin matrix polypeptide with in vitro chondrogenic activity. *J. Biol. Chem.* 266:8609–8618, 1991.
7. Pettipher, E. R., I-Eggs, G. A., Henderson, B.: Interleukin-1 induces leukocyte infiltration and cartilage proteoglycan degradation in the synovial joint. *Proc. Natl. Acad. Sci. U.S.A.* 83:8749–52, 1986.
8. Saklatvala, J.: Tumor necrosis factor a stimulates resorption and inhibits synthesis of proteoglycan in cartilage. *Nature* (London) 322, 547, 1986.
9. Sandy, J., Neame, P., Boynton, R., Flannery, C. R-: Catabolism of aggrecan in cartilage explants. *J. Biol. Chem.* 266: 8198–8192, 1991.
10. Saklatvala, J.: Biological regulation of the chondrocytes. *Adorphe, M.* 191–201, 1992.
11. Nietfield, J J, Huber-Bruning, O and Bylsma, J W J. Cytokines and proteoglycans in Proteoglycans (Jolles, P. ed.) Birkhauser, Berlin, 1994.
12. Lohmander, L. S., Saxne, T., Heinegard, D.: Release of cartilage oligomeric protein. *Ann. Rheum. Dis.* 53: 8–13, 1994.
13. Fisher, L,. W., Termine, J. D., Dejter, S. W., Whitson, S. W., Yanagishita, M., Kimura, J. H., Hascall, V. C., Kleinman, H. K., Hassell, J. R., Nilsson, B.: Proteoglycans of Developing Bone. *J. Biol. Chemi.* 258:6588–6594, 1983.
14. Recklies, A. D., White, C., Baillargeon, L.: The intracellular localization of cartilage GP-39 characterizes the superficial cell layers of articular cartilage. *Trans Ortho. Res. Soc.* 40:458, 1994.
15. Kraus, V N M, Hughes, C. E., Neame, P., Heinegard, D., Dudhia, J., Hardingham T., Caterson, B.: Production and characterization of a novel monoclonal antibody to the G3 domain of cartilage aggrecan. *Trans Ortho. Res. Soc.* 42:763, 1996.
16. Heinegard, D., Peterson, I., Boegard, Dahlstrom, J., Sbensson, B., Poole, A. R., Ionescu, M., Saxne, T.: *Trans Ortho. Res. Soc.* 42, 219, 1996.
17. Poole, A. R., Pidoux, I., Reiner, A., Choi H. Rosenberg, L. C. Association of an extracellular protein (chondrocalcin) with the calcification of cartilage in endochondral bone formation. *J. Cell. Biol.* 98: 54–60, 1984.
18. Stefanovic-Racic, M., Startler, J., Georgescu, H. I., Evans, C. R: Nitric oxide synthesis and its regulation by rabbit synoviocytes. *J. Rheumatology* 21:10, 1994.
19. Wakitani, S., Goto, T., Pineda, S. J., Young, R., Mansour, J., Caplan, A., Goldberg, V.: Mesenchymal cell-based repair of large, full-thickness defects of articular cartilage. *J. Bone and Joint Sur. Inc.* 76:A, 1994.
20. Martel-Pelletier, J., Zafarullah, M., Kodama, S., Pelletier, J. P.: In vitro effects of interleukin 1 on the synthesis of metalloproteinases, TMD, plasminogen activators and inhibitors in human articular cartilage. *J Rheumatol* 18(Suppl. 27), 80, 1991.
21. Trippel, S. T., in Biological regulation of the chondrocytes. *Adolphs, M* 161–190, 1992.
22. Joyce, M. E., Roberts, A. B., Sporn, M. B., Bolander, M. E.: Transforming growth factor-beta and the initiation of chondrogenesis and osteogenesis in the rat femur. *J Cell Biol.* 110: 2195–2202, 1990.
23. Majumdar, M P, Haynesworth, S E, Thiede, M A, Marshak, D M, Caplan, Al & Gerson, S L Culture-expanded human mesenchymal stem cells (MSCS) express cytokines and support hematopoiesis in vitro. *Blood* 86, 494a, 1995.
24. Majumdar, M. P., Haynesworth, S E, Thiede, M A, Marshak, D M, Caplan, Al & Gerson, S L: Culture-expanded human mesenchymal stem cells (MSCs) express cytokines and support hematopoiesis in vitro. submitted for publication.
25. Barry, F. P., Rosenberg, L. C., Gaw, J. U., Koob, T. J., Neame, P. J.: *J Biol. Chem.,*270: 20516–20524, 1995.
26. Barry F P, Neame, P J, Sasse, J and Pearson, D Length variation in the keratan sulfate domain of mammalian aggrecan, *Matrix Biology* 14: 323–328, 1994.
27. Sandy, J., Boynton, R., & Flannery, C. Analysis of the catabolism of aggrecan in cartilage explants by quantitation of peptides from the three globular domains *J Blot Chem.* 266: 8198–8205, 1991.
28. Flannery, C R, Stanescu, V., Morgelin, M., Boynton, R., Gordy, J., and Sandy, J. Variability in the G3 domain content of bovine aggrecan from cartilage extracts and chondrocyte cultures. *Arch. Biochem. Biophys.* 297: 52–60, 1992.
29. Hampton, B., Burgess, W. H., Marshak, D. R., Cullen, K J. and Perdue, J. F. Purification and characterization of an insulin-Eke growth factor H variant from human plasma. *J Biol. Chem.* 264: 19155–19160, 1989.
30. Marshak, D. R. and Binns, G. E. 1990. Protein sequence analysis by plasma desorption mass spectrometry. in *Current Research in Protein Chemistry* (J. J. Villafranca, Ed.), Academic Press, New York, 127–138.
31. Schwarz, H., Tuckwell, J., Lotz, M.: Identification of a new member of the human nerve growth factor/tumor necrosis factor receptor family. *Gene* 134:295–298, 1993.
32. Thonar, E., Manicourt, D. M., Williams, J., Lenz, M. E., Sweet, M. B. E., Schnitzer, T. J., Otten, L., Glant, T., Kuettner, K. E.: Circulating Keratan Sulfate: A marker of cartilage proteoglycan catabolism in osteoarthritis. *J Rheum.* 18:(Suppl. 27), 1991.
33. Pond, M. J., N G.: Experimentally-induced osteoarthritis in the dog. *Ann. Rheum. Dis.* 32:387–388, 1973.
34. Moskowitz, R- W., Davis, W., Sammarco, J.: Experimentally induced degenerative joint lesions following partial meniscectomy in the rabbit. *Arthritis Rheum.* 16:397–405, 1973.
35. Moskowitz, R- W.: Osteoarthritis. *Diagnosis and Medical/Surgical Management,* 213–232, 1992.
36. Ala-Kokko, L., Baldwin, C T, Moskowitz, R W & Prockopp, D J Single base mutation in the type II procollagenase (COL2A1) as a cause of primary osteoarthritis associated with mild chondrodysplasia *Proc. Natl. Acad. Sci. USA,* 87, 6565–6568, 1990.
37. Eyre, D R, McDevitt, C A, Billingliam, M E J, and Muir, H. Biosynthesis of collagel and other matrix proteins by articular cartilage in experimental osteoarthritis. *Biochem. J* 188:823–837, 1980.
38. Matyas, J. and Sandell, L. J. Discoordinate gene expression of aggrecan and type 11 collagen mRNA in experimental osteoarthritis. *Orth. Res. Report*, Univ. Washington, Seattle, pp 46, 1995.
39. Yu, L P, Smith, G N, Brandt, K D. Reduction of the severity of canine osteoarthritis by prophylactic treatment with oral doxycycline. *Arthritis. Rheum.* 35:1150–1159, 1992.

40. Pelletier, J P and Martel-Pefletier, J. Protective effects of corticosteroids on cartilage lesions and osteophyte formation in the Pond-Nuki dog model of osteoarthritis. *Arthritis Rheuni.* 32: 181–193, 1989.
41. Thiede, M. A., Majumdar, M. P., Longin, K, Hardy, W., Gerson, S., Marshak, D. R., Storb, R and Sandmeier, B. M. Reinfuision of ex vivo-expanded, retrovirus-transduced, autologous mesenchymal stem cells (MSCs) into irradiated dogs. *Blood* 86: 112a, 1995.
42. Lazarus, H M, Haynesworth, S E, Gerson, S L, Rosenthal N S and Caplan, A l. Ex vivo expansion and subsequent infusion of human bone-marrow-derived stromal progenitor cells (mesenchymal progenitor cells): implications for therapeutic use. *Bone Marrow Transplantation* 16: 557–564, 1995.
43. Shapiro, F., Koide, S., and Glimcher, M. J. J. *Bone and Joint Surg.* 75A, 532–553, 1993.
44. Wakitani, S., Goto, T., Pineda, S. J., Young, R. G., Mansour, J. M., Caplan, A. I., and Goldberg, V. M. J *Bone and Joint Surg.* 76A, 579–52, 1994.

What is claimed is:

1. A method for regenerating articular cartilage defects in a host in need thereof, comprising administering to said host cultured human mesenchymal stem cells, said human mesenchymal stem cells having a fibroblastic morphology.

2. The method of claim 1, wherein the method further comprises administering a biomatrix material.

3. The method of claim 1, wherein the method further comprises administering a contracting agent.

4. The method of claim 1, wherein the method further comprises administering a chondrogenesis promoting factor.

5. The method of claim 4, wherein the factor is TGF-β3.

6. The method of claim 1, wherein the method further comprises administering IL-1 inhibitors.

7. The method of claim 1, further comprising administering osteochordral precursor cells.

8. The method of claim 1, wherein the cartilage defect comprises an articular cartilage injury.

9. The method of claim 1, wherein the biomatrix is selected from the group consisting of a collagen gel, a chemically cross-linked collagen gel, a fibrin gel, a fibrin glue, and an autologous fibrin gel.

10. The method of claim 8, wherein said administering is through arthroscopic injection.

11. The method of claim 1, wherein said cartilage defect comprises a lesion on an articular surface.

12. The method of claim 11, wherein the human mesenchymal stem cells are in a liquid suspension.

13. The method of claim 12, wherein said administering is by injection directly into a synovial cavity in proximity to a lesion.

14. The method of claim 12, wherein said liquid suspension further comprises serum or buffered saline.

15. The method of claim 2, wherein the cartilage defect comprises loss of cartilage at a joint.

16. The method of claim 15, wherein the biomatrix is a molded gel.

17. The method of claim 16, wherein said administering is by direct application to the joint surface.

18. A process for treating a cartilage defect resulting from osteoarthritis, comprising administering to a host in need thereof human mesenchymal stem cells in an amount effective to repair the cartilage defect, said human mesenchymal stem cells having a fibroblastic morphology.

19. The process of claim 18, wherein the amount of human mesenchymal stem cells is in the range of from about $0.1 \times 10^8$ to about $1 \times 10^8$ cells.

* * * * *